United States Patent
List

(10) Patent No.: US 10,278,621 B2
(45) Date of Patent: May 7, 2019

(54) ANALYTICAL SYSTEM FOR EXAMINING A BODY FLUID AND METHOD FOR THE OPERATION OF AN ANALYTICAL SYSTEM

(71) Applicant: Roche Diabetes Care, Inc., Indianapolis, IN (US)

(72) Inventor: Hans List, Hesseneck-Kailbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 172 days.

(21) Appl. No.: 15/409,891

(22) Filed: Jan. 19, 2017

(65) Prior Publication Data
US 2017/0127986 A1 May 11, 2017

Related U.S. Application Data

(63) Continuation of application No. 14/335,062, filed on Jul. 18, 2014, now Pat. No. 9,573,761, which is a (Continued)

(30) Foreign Application Priority Data

Jan. 18, 2012 (EP) .................................... 12151541

(51) Int. Cl.
*A61B 5/145* (2006.01)
*A61B 5/1455* (2006.01)
(Continued)

(52) U.S. Cl.
CPC ........ *A61B 5/14532* (2013.01); *A61B 5/1455* (2013.01); *A61B 5/1468* (2013.01); (Continued)

(58) Field of Classification Search
CPC ........ A61B 2562/0295; A61B 5/15029; G01N 33/4875
See application file for complete search history.

(56) References Cited

U.S. PATENT DOCUMENTS

| | | |
|---|---|---|
| 2003/0032190 A1 | 2/2003 | Brown et al. |
| 2004/0092995 A1 | 5/2004 | Boecker |

(Continued)

FOREIGN PATENT DOCUMENTS

| | | |
|---|---|---|
| EP | 1 160 587 A1 | 12/2001 |
| EP | 0 784 204 B1 | 8/2003 |

(Continued)

*Primary Examiner* — Paul S Hyun
(74) *Attorney, Agent, or Firm* — Woodard, Emhardt, Henry, Reeves & Wagner, LLP

(57) ABSTRACT

An analytical system for examining a body fluid and a method of operation of an analytical system, typically for blood sugar tests, including an exchangeable magazine (18) as a consumable, which includes a plurality of magazine units (24) that are each provided with at least one analytical aid (32, 34) and with a transport element (28), a hand-held device (12) having a magazine guide (16) for receiving the magazine (18), a transport mechanism (48) that engages on the transport elements so as to transport the magazine in steps in the magazine guide, including a positioning mechanism (50) for positioning an active magazine unit in a predefined functional position, wherein retaining elements (52, 54) of the positioning mechanism can be brought into engagement with transport elements of the magazine.

11 Claims, 3 Drawing Sheets

Related U.S. Application Data continuation of application No. PCT/EP2013/050697, filed on Jan. 16, 2013.

(51) Int. Cl.
    *B65G 1/133*     (2006.01)
    *A61B 90/00*     (2016.01)
    *A61B 5/1468*     (2006.01)
    *A61B 5/157*     (2006.01)
    *G01N 21/78*     (2006.01)

(52) U.S. Cl.
    CPC ............ *A61B 5/157* (2013.01); *A61B 90/361* (2016.02); *B65G 1/133* (2013.01); *G01N 21/78* (2013.01); *A61B 2560/0431* (2013.01); *A61B 2560/06* (2013.01); *A61B 2562/0295* (2013.01)

(56) References Cited

U.S. PATENT DOCUMENTS

| | | |
|---|---|---|
| 2005/0154410 A1 | 7/2005 | Conway |
| 2006/0157362 A1 | 7/2006 | Schrage |
| 2010/0216246 A1 | 8/2010 | Konya et al. |
| 2012/0063970 A1 | 3/2012 | List et al. |

FOREIGN PATENT DOCUMENTS

| | | | |
|---|---|---|---|
| EP | 2 130 493 A1 | 12/2009 | |
| WO | WO 2006/004859 A2 | 1/2006 | |
| WO | WO 2010/094426 A1 | 8/2010 | |

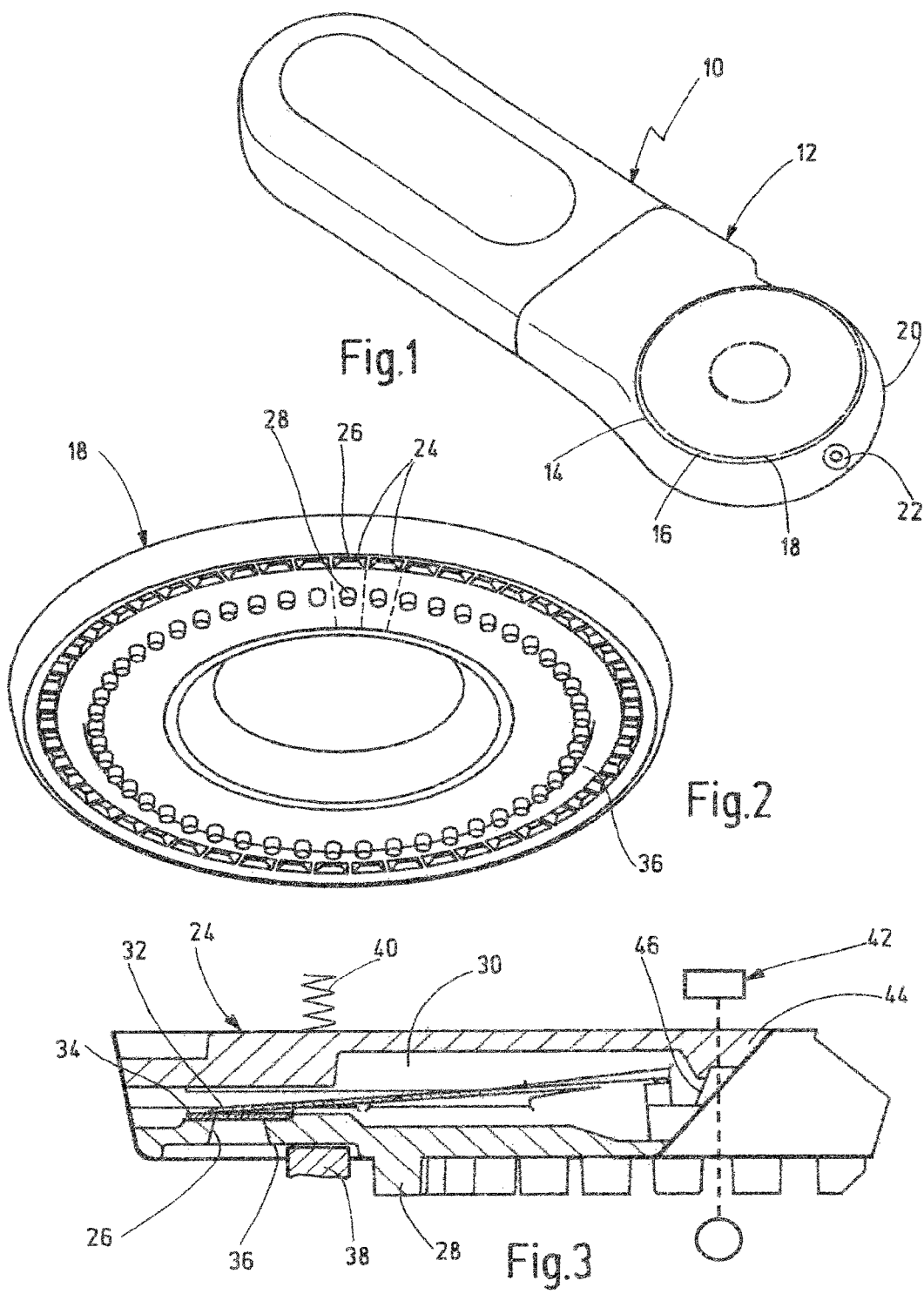

ANALYTICAL SYSTEM FOR EXAMINING A BODY FLUID AND METHOD FOR THE OPERATION OF AN ANALYTICAL SYSTEM

CROSS-REFERENCE TO RELATED APPLICATIONS

This application is a continuation of U.S. patent application Ser. No. 14/335,062 filed Jul. 18, 2014, which is a continuation of PCT Application PCT/EP2013/050697, filed Jan. 16, 2013, which claims priority to European application number 12151541.5, filed Jan. 18, 2012, all of which are hereby incorporated by reference.

BACKGROUND

The invention relates to an analytical system for examining a body fluid, typically for blood sugar tests, with an exchangeable magazine as a consumable, which comprises a plurality of magazine units that are each provided with at least one analytical aid and with a transport element, a hand-held device having a magazine guide for receiving the magazine, and a transport mechanism that engages on the transport elements typically arranged in a ring shape, so as to transport the magazine in steps in the magazine guide. The invention further relates to a method for the operation of an analytical system.

In portable hand-held systems for automatic collection and measurement of body fluids, magazines with a plurality of disposable measurement units are increasingly being used in order to improve user friendliness. Compared to conventional measurement devices, these involve increased outlay in terms of mechanical movements. In an attempt to minimize the overall size of such systems, the structures of the magazine and of the device, which have to match each other, are becoming ever smaller, even though the tolerances of the individual parts do not decrease on the same scale. There are therefore ever greater demands on the positioning. The individual miniaturized tests require both a high level of precision and accuracy in terms of the position relative to the evaluation system and also a high degree of robustness in terms of the stability of the position during the measurement. The latter applies especially in the case of electrically evaluated tests, because each movement of contacts through which current flows leads to signal noises, and this disrupts the evaluation or makes it completely impossible. However, optical systems are also extremely sensitive to changes of position during ongoing measurement. A further aspect to be taken into account is that the magazine, as a consumable, should remain limited to the structures and components essential for the test procedure, so that the production costs can be kept as low as possible.

An analytical system of the type in question with a magazine in the form of a circular disk is mentioned in WO 2010/094426. It is proposed there that the analytical system can have a corresponding transport device which interacts with transport elements of the magazine in order to further transport the magazine units. Said document also discloses a method for producing such a magazine, to which reference is here made.

Generally speaking, concepts that involve accommodating an annular magazine over the ring center in the device, and leaving the precision of the movements to the device parts, lead to a very complex and expensive configuration since, in addition to the inevitable dimensional deviations of the magazine disk itself, many other structures of the device, which likewise necessarily have dimensional deviations and in some cases also a degree of running play, are included in the tolerance chain of the positioning. The six degrees of freedom of movement of the magazine can thus be brought under control only with an unjustifiable amount of effort.

Proceeding from this, an object of the invention is to further improve the systems and methods proposed in the prior art and to ensure precise positioning of the test units and magazine units, such that the requirements in terms of mechanics and measurement are satisfied even in the case of considerable miniaturization. At the same time, the magazine should be able to be exchanged and also transported by simple means.

BRIEF SUMMARY

An aspect of the invention is based on the concept of giving utmost priority to an exact positioning during measurement. Accordingly, a positioning and fixing mechanism of the device is provided, by which an active magazine unit ready for use is positioned and fixed (maintained in position) in a predefined functional position, wherein the positioning mechanism has retaining means, and the retaining means can be brought into engagement with one or more of the transport elements of the magazine. The retaining means and the transport elements can thus be brought to a position of mutual engagement, in which magazine transport is interrupted and, at the same time, a precise position with respect to the device is maintained, such that in particular a relative position to a measurement unit or to a finger receiver or the like can be maintained reproducibly with small tolerances.

Advantageously, retaining means engage with a form fit on the transport element of the active magazine unit located in the functional position and thus block a movement of the magazine in at least one direction. It is thereby possible to maintain short distances to relevant reference points and thus also minimize the variations of such distances. It should also be noted here that, especially in mass production methods, such as injection molding of consumables, the deviations correlate with the size of a dimension.

Advantageously, the transport elements are arranged in a ring shape, while the retaining means, in the engagement position, are in form-fit engagement with two transport elements which typically lie diametrically opposite each other or are at least arranged far from each other, and they thus prevent a movement in several degrees of freedom. It is also conceivable that the transport elements engaged by retaining means do not lie on an axis but instead at an obtuse angle with respect to the magazine center.

Two retaining means can be provided, a first retaining means typically being fixed on the device, and a second retaining means being movable in the device.

In a typical embodiment, a bearing point which is arranged rigidly in the device is used as retaining means for receiving the transport element of the active magazine unit. In this way, a fixed reference point in the device is created, such that further device mechanisms can be oriented relative thereto. This can be advantageously achieved, also in terms of the subsequent transport procedure, in that the retaining means have a laterally open bearing eye into which the transport element of the magazine unit located in the functional position can move in and back out again in a linear movement.

The magazine is advantageously annular and is mounted so as to be movable with limited pivoting about an axis typically extending through the transport element of the active magazine unit and eccentric with respect to the ring axis or central axis (technical mid-line) of the magazine, such that a defined device structure can be used also for the onward indexing of the magazine units during a transport phase and the magazine is not entirely freely movable.

In order to permit a specifically switchable engagement, it is advantageous if the retaining means comprise a gripper movable between an engagement position, in which it is in engagement with a transport element, and a release position, in which it is at a distance therefrom, and which serves to secure the position of the magazine.

In order to further reduce a positioning play, the gripper, in its engagement position, should press against at least one transport element under the application of a force. In principle, it is also possible that the gripper, in its engagement position, engages between two transport elements and presses against these under the application of a force.

It is also expedient if the transport mechanism has a control means, in particular a cam gear for controlling the movement of the gripper. In this way, if appropriate with only one drive source, for example an electric motor, it is possible for the transporting and the positioning processes to be controlled jointly and adapted to each other.

To make magazine exchange easier, it is advantageous if the gripper is coupled via an adjustment means to a lid that closes the magazine guide, such that the gripper moves to the release position when the lid is opened, as a result of which five of the six degrees of freedom of the magazine are freed and the user can exchange the magazine without problem.

For preliminary positioning, it is particularly advantageous if the magazine guide has three supporting portions which span one plane and which serve to support a plane guide surface of the magazine.

A further improvement in the positioning accuracy can be achieved if the magazine, movable to a limited extent in a bearing plane, is under the influence of a force perpendicular to the bearing plane. It is advantageous if the vertical forces on the work plane of the magazine are generated by springs in the lid that close the work space of the magazine. It is also expedient if the vertical forces in total are as great as the product of the mass of the magazine and of the maximum permissible impact acceleration that does not yet impair a measurement.

Advantageously, the transport mechanism is provided with gear elements which superpose a limited linear release movement on an eccentric pivoting movement of the magazine, wherein at least one transport element is disengaged from a retaining means fixed on the device. In this way, a ring magazine in particular can be alternately transported and positioned in steps. The retreat movement typically takes place in the plane defined by the path of the pivoting movement. A movement perpendicular to this plane is typically to be avoided.

In connection with a combined rotary movement and linear movement, it is also advantageous if the transport mechanism has a slide which is movable on an elliptical path and which, in a portion of its path of movement, engages on a transport element, and if the magazine guide has arc-shaped directing contours for the transport elements, wherein the directing contours control a release movement of the transport element deviating from a circular path.

To test the usability of the magazine units, a test unit, particularly in the form of a light barrier scanning a sealing film, is advantageous.

The magazine is typically designed as a ring magazine, in particular as a circular disk magazine with magazine units distributed in the circumferential direction. Such a magazine typically has a diameter of less than 100 mm, optionally of less than 70 mm, and comprises a multiplicity of analytical test means (e.g. piercing and/or analyzing units) in associated magazine units, for example numbering 10 to 100 units in total. It is also advantageous if the transport elements are formed by a ring of projections (e.g. pins) or depressions oriented axially parallel or radially on a respective magazine unit.

In a typical combination, the retaining means have a bearing point, fixed on the device and provided for one of the transport elements, and also a gripper engaging on a further transport element at a distance from the bearing point.

Regarding the method, a magazine which is typically a consumable is inserted in a magazine guide of a hand-held or portable device, wherein the magazine comprises a plurality of magazine units that are each provided with at least one analytical aid and with a transport element, that the magazine is transported in steps in the magazine guide by a transport mechanism that engages on the transport elements typically arranged in a ring shape, and that retaining means of a device-side positioning mechanism are brought into engagement with transport elements of the magazine, wherein an active magazine unit provided for use is positioned or fixed in a predefined functional position in the device.

To ensure very precise positioning at the measurement site, it is advantageous if retaining means engage on a transport element in the area of the active magazine unit and a movement of the magazine in at least one direction is prevented. It is also advantageous if, by blocking at least one transport element located (as far as possible) away from the active magazine unit, the magazine is kept immovable, typically by a gripper, during a positioning phase.

In the positioning according to the invention, the low geometry of the magazine together with its comparatively large area is exploited in order to assign the magazine a working plane. This is advantageously achieved by the large area of the magazine resting on three device-side support surfaces and being held there by forces acting perpendicularly thereto. In this way, three degrees of freedom are already defined.

For further fixing of position, a bearing between tips is used in order to retain the magazine in a spatially defined manner along an axis. Two of the retaining means are brought into contact with suitable transport elements of the magazine units, wherein the retaining means that engages on the momentarily active magazine unit fixes two further degrees of freedom, while the retaining means that engages diametrically opposite thereto or as far away as possible therefrom fixes the last (sixth) degree of freedom. It is also conceivable for engagement to take place between two transport elements as far away as possible from the active magazine unit, such that a statically defined bearing is likewise obtained, e.g. by a wedge piece engaging between two transport elements such that these rest on the wedge flanks.

The retaining means near the measurement site is advantageously formed by a rigid device structure, and the retaining means remote from the measurement site is in the form of a movable device structure. The latter should be exposed to a force corresponding to the maximum permissible impact load, in order to ensure an impact-resistant positioning.

In order, when necessary, to move the magazine from this fixed position by one further test unit in a subsequent transport phase, the degrees of freedom in which the magazine is to be moved are released in succession according to the invention, wherein the interference friction caused by the pressure of the magazine against its working plane is exploited in order to ensure that, despite the release of degrees of freedom, the magazine is prevented from leaving its position in an uncontrolled manner.

The annular magazine is advantageously mounted on the transport element of the active magazine unit eccentrically to the central axis (technical mid-line) of the rotationally symmetrical magazine, such that a limited pivoting movement of the whole magazine is possible in the transport phase.

For onward indexing of the magazine units, the magazine is advantageously pivoted about an individual bearing point fixed on the device and then released therefrom, wherein one transport element of the respective active magazine unit is initially guided in the bearing point and then comes free, and wherein the transport elements of the other magazine units are moved against a directing contour of the magazine guide free from the bearing points.

BRIEF DESCRIPTION OF THE DRAWINGS

The invention is explained in more detail below, and an illustrative embodiment is depicted in the drawings, in which:

FIG. 1 shows a perspective view of a diagnostic analysis system comprising a hand-held device and, inserted in the latter, a magazine for analytical aids;

FIG. 2 shows a perspective view of the magazine designed in the shape of a ring or a disk;

FIG. 3 shows a magazine unit in a cutaway radial section of the magazine;

DETAILED DESCRIPTION

Figure 4:
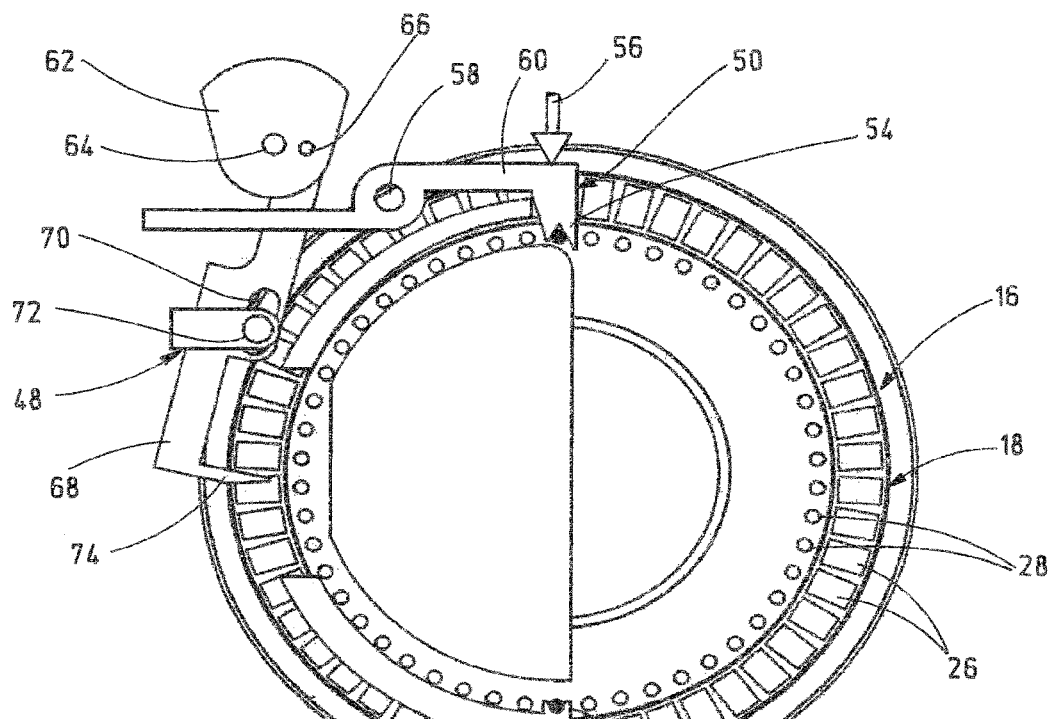
FIG. 4 shows a plan view of a transport mechanism in conjunction with a positioning mechanism for the magazine at a first position.
Figure 5:
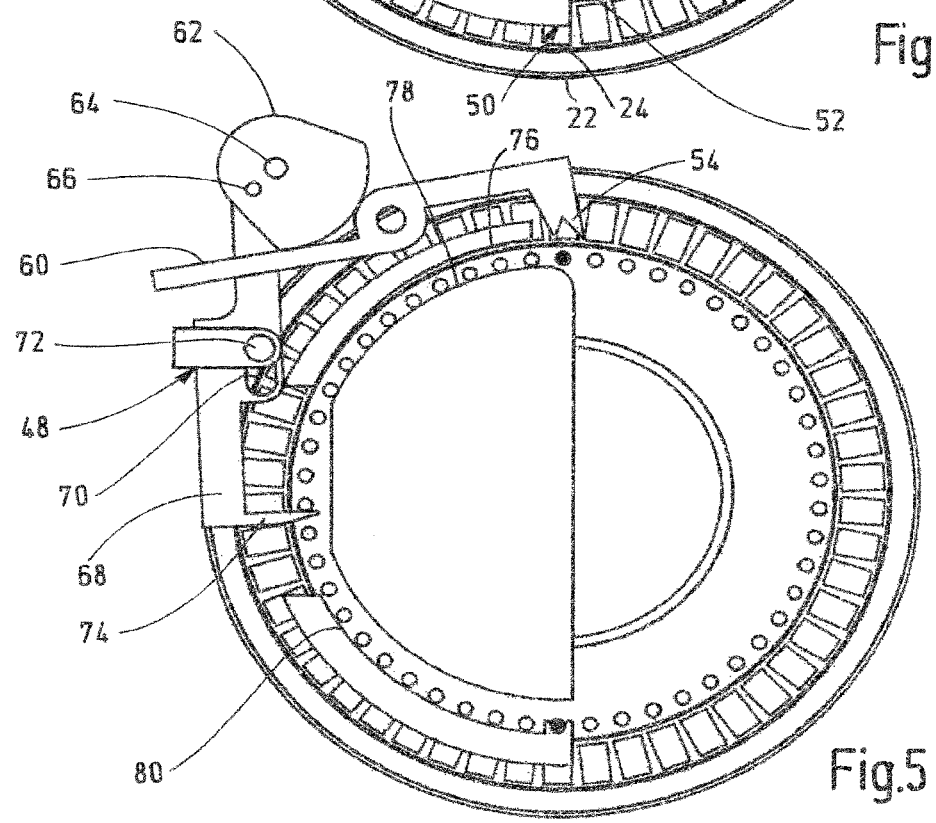
FIG. 5 shows a plan view of a transport mechanism in conjunction with a positioning mechanism for the magazine at a second position.

The analysis system 10 shown in FIG. 1 can be held in the hand of a test subject and be used on the spot for blood sugar measurements. For this purpose, the instrument comprises a portable or hand-held device 12 with a magazine guide 16 which can be closed by means of a lid 14 and which receives a disposable annular magazine 18. An application opening 22 on which the test subject places a finger is provided on the housing 20 of the device 12 in order to collect a blood sample for glucose determination by means of a skin incision.

The ring-shaped annular magazine 18 shown in FIG. 2 has a multiplicity of magazine units 24 distributed in the circumferential direction. Each magazine unit 24 has a measurement window 26 and a transport element 28 in the form of a pin protruding from the underside of the magazine. The transport elements 28 arranged in a ring shape permit step-by-step indexing and defined positioning of the individual magazine units 24 in a functional position in front of the application opening 22.

As is shown in FIG. 3, a piercing element 32 and a test element 34 are located in the magazine chamber 30 of each magazine unit 24. In the functional position, the piercing element 32 can be pushed out radially by means of a reciprocating piercing drive (not shown) so that, when the skin is pierced, a small amount of blood is taken up in a capillary channel and is transferred to the test field 34. The test field 34 is provided with a test chemical that responds to the analyte (glucose) with a change of color and can be optically scanned via the measurement window 26 by means of a photometric measurement unit (not shown) transversely with respect to the annular plane. The active magazine unit is positioned as precisely as possible in the functional position in front of the application opening 22 and over the measurement unit. For this purpose, the magazine 18 has, next to the transport elements 28, a plane surface 36 which is held at a defined measurement distance by a device-side three-point bearing on hard support humps 38, such that the optical beam path is reproducible. In order to keep the position tolerances low, a spring 40 presses on the upper face of the magazine 18 on the opposite side of each of the three support humps 38 in a trigonal planar arrangement.

In order to ensure, particularly upon exchange of a magazine, that used piercing elements are not re-used, a device-side light barrier 42 is provided which passes a beam through a transparent area 44 of the magazine units 24. A sterile film or sealing film 46 that closes off the magazine chamber 30 from the piercing drive is thus scanned, the state of use being directly detectable from the destruction of the film.

FIGS. 4 to 7 illustrate the sequence of movement for the onward indexing and defined positioning of the magazine units 24 of the magazine 18 in the device 12 (not itself shown). For this purpose, a device-side transport mechanism 48 is coupled to a positioning mechanism 50 (fixing mechanism) of the device, in order to satisfy said functions by a manipulation of the transport elements 28 of the magazine 18. Both the transport mechanism 48 and also the fixing mechanism thus engage on the transport elements 28 of the magazine 18.

FIG. 4 shows a magazine position in which a magazine unit 24 is held fixedly in the functional position. For this purpose, the positioning mechanism 50 is provided with retaining means 52, 54 which are arranged on the device and which are in releasable form-fit connection with two diametrically opposite transport elements 28 (highlighted in black in the drawing) of the magazine 18.

One of the retaining means is formed by a laterally open bearing eye 52 which, as a bearing point fixed on the device, engages half way round the transport element 28 of the magazine unit 24 located in the functional position. On account of the short distance to the active measurement window 26 of this magazine unit 24, a low position tolerance is obtained. Self-locking with respect to transverse movements is effected by the steep flanks of the bearing eye.

Thus, the magazine 18 could only still rotate about the fixed pin or retreat linearly from the bearing eye. In order also to prevent a movement in these remaining degrees of freedom, a prismatic gripper 54 engages as retaining means on the diametrically opposite pin. This gripper 54 is urged by a restoring force in the direction of the arrow 56, for example by means of a spring. The restoring force should be greater than the frictional forces that are caused by the spring suspension of the magazine 18 on the three support humps 38. In order to permit coupling to the transport mechanism 48, the gripper 54 is arranged at one end of a two-armed gripper lever 60, which is able to pivot about the axis 58.

In this arrangement, the active magazine unit 24 is located geometrically precisely in front of the measurement unit in the functional position. The gripper 54, as the only movable structure involved in this (and, for example, requiring a clearance for its movement), is at a distance, corresponding to the diameter of the ring of pins, much farther away from the position-determining bearing point than the measurement unit which is located in the area of the measurement window 26 and which therefore has a precisely defined optical transmission path.

However, the self-locking design of the retaining means 52, 54 for the pins or transport elements 28 suppresses onward transport of the annular magazine 18 to the next magazine unit 24. In order to permit this transport, the gripper 54 with its catching prism has to be lifted by the transport mechanism 48 actively against the restoring force 56 from its engagement position to its release position, as is shown step by step in FIGS. 5 to 7.

For the movement coupling, the transport mechanism 48 has a control cam 62 as cam gear which sits on the output shaft 64 of a motor and drives an excavator lever 68 via a crank pin 66, while the circumferential contour of the control cam 62 actuates the gripper lever 60. The excavator lever 68 is mounted over an oblong hole 70 such that it can move to and fro in a generally elliptical movement on a bearing pin 72 fixed to the device and can rotate about this. In the course of this movement, a blade-shaped slide 74 engages on the transport elements 28 and, in interaction with arc-shaped directing contours 76, 78, 80 (FIG. 5) of the magazine guide 16, effects a transport step to the next magazine unit 24.

Figure 6:
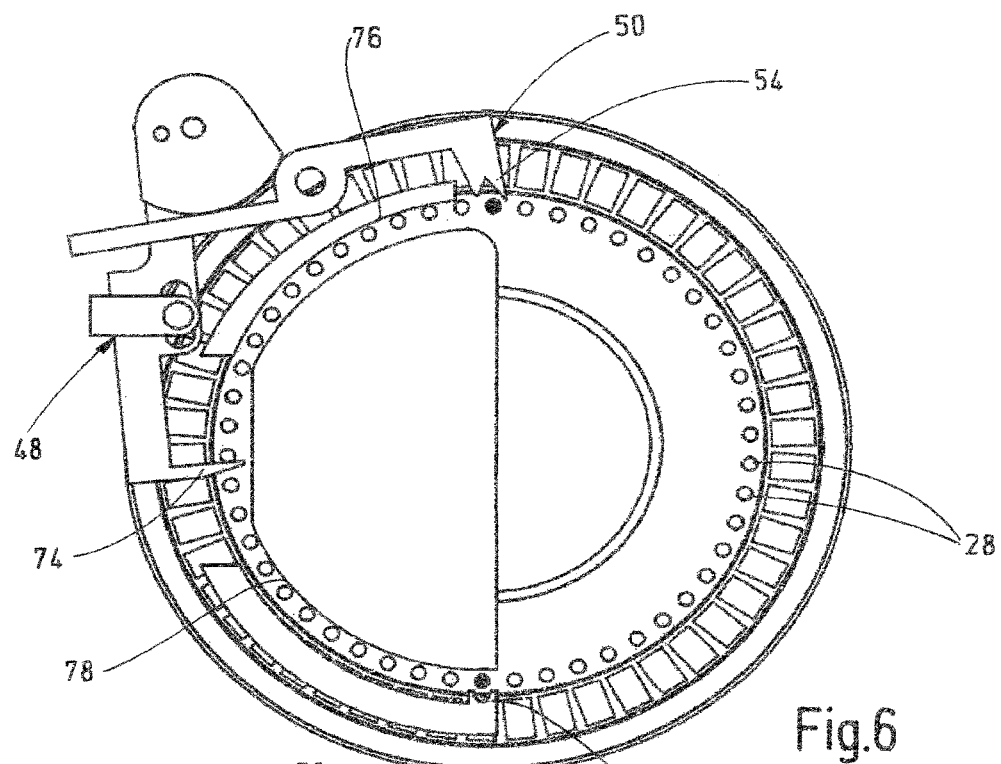
FIG. 6 shows a plan view of a transport mechanism in conjunction with a positioning mechanism for the magazine at a third position.
Figure 7:
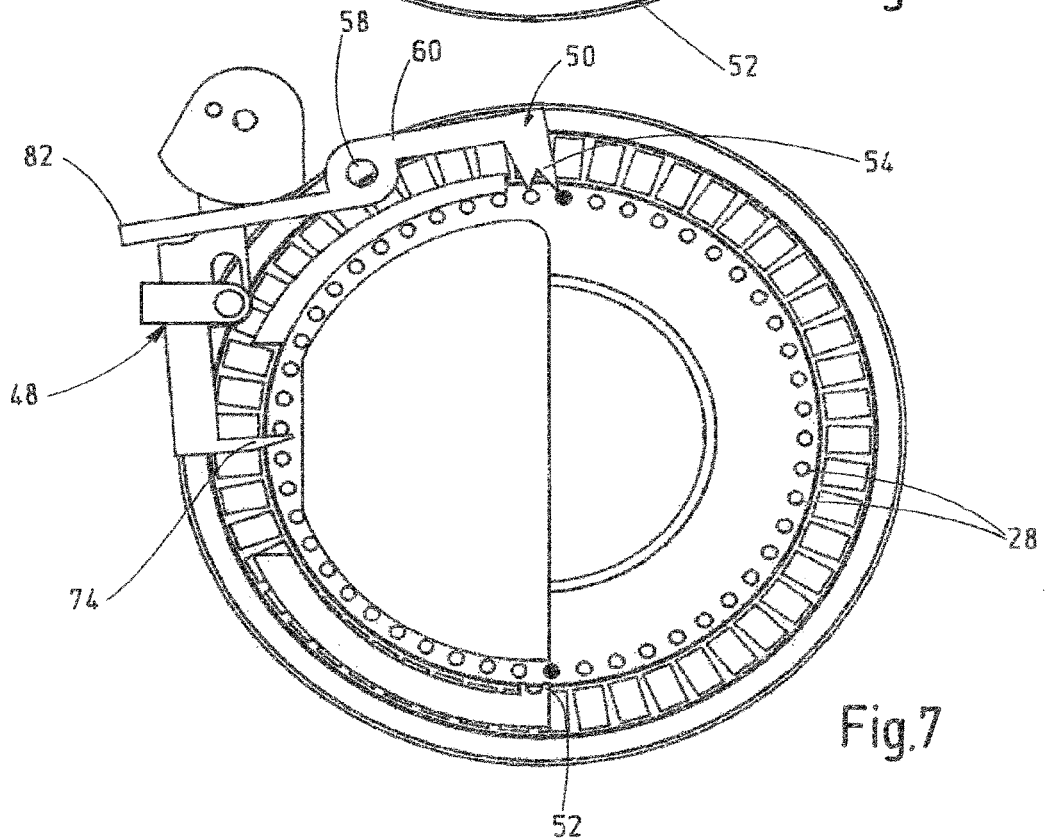
FIG. 7 shows a plan view of a transport mechanism in conjunction with a positioning mechanism for the magazine at a fourth position.

In the initial phase (shown in FIG. 5) of the onward indexing, the gripper 54 is first of all moved to its release position by the control cam 62. Simultaneously with this, the slide 74 is guided on an elliptical path into the ring of transport elements 28 such that one of the latter is gripped. As a result of the strongly eccentric engagement of this slide movement relative to the friction of the pressing springs 40 against the three support surfaces of the magazine 18, a torque arises that allows the whole magazine 18 to pivot (clockwise in FIG. 5) about the transport element located in the bearing eye 52. This pivoting movement is limited by the arc-shaped directing contour 76 against which the ring of transport elements 28 runs (FIG. 6). As soon as the pivoting movement is stopped, only a linear degree of freedom still remains available, which allows the magazine to retreat from the bearing eye 52 until transport elements 28 once again abut the directing contour 78, such that in the final phase only a rotation of the whole magazine 18 is still possible (FIG. 7). After this rotation has advanced one magazine division, the slide 74 on its elliptical path disengages from the transport elements 28, and the gripper 54 drops again onto the next transport element located in its catch area, as a result of which the magazine 18 also moves once again into the bearing eye 52. The magazine 18 is thus once again clearly positioned in front of the measurement unit, but with a new magazine unit 24.

The above-described mechanism never completely frees the magazine 18. Upon removal of a magazine from the system, the gripper 54 would pivot still further into the magazine guide 16 under the restoring force 56, as a result of which the insertion of a new magazine would be impeded. In order to avoid this, the gripper lever 60 is lengthened and, at its free end 82, is coupled to the device lid 14 via an adjustment means (not shown). The adjustment means, e.g. a connecting rod, is moved by the opening device lid 14 and actuates the gripper lever 60, such that the gripper 54 moves to its release position, specifically without engaging the slide 74.

This allows the user to place a new magazine into the device without considering the angular orientation of the magazine 18. To ensure that the magazine 18 does not remain in an intermediate position and is not secured in this position by the once again inwardly pivoting gripper 54, a transport cycle should first take place after the closure of the housing lid 14. It should also be ensured, when fitting an already used magazine, that no used piercing elements 32 are used, so as to rule out a danger of infection. For this purpose, the transport cycles should be carried out until, by means of the light barrier 42 as test unit, an unused magazine unit 24 is detected in the functional position.

The invention claimed is:

1. An analytical system for examining a body fluid, the system comprising: an exchangeable magazine comprising a plurality of magazine units that are each provided with at least one analytical aid and a transport element, a hand-held device having a magazine guide for receiving the magazine, a transport mechanism that engages on the transport elements which are optionally arranged in a ring shape, so as to transport the magazine in steps in the magazine guide, and a fixing mechanism for positioning an active magazine unit of the plurality of magazine units in a predefined functional position, wherein the fixing mechanism comprises retaining means which can be brought into engagement with the transport elements of the magazine units, wherein the retaining means engage on a first transport element corresponding to the transport element of the active magazine unit and on a second transport element that is located at a distance from the active magazine unit.

2. The analytical system of claim 1, wherein the retaining means engage with a form fit on the first transport element of the active magazine unit and block a movement of the magazine in at least one direction.

3. The analytical system of claim 1, wherein the magazine is annular and is mounted so as to be movable with limited pivoting about an eccentric axis that extends through the first transport element of the active magazine unit.

4. The analytical system of claim 1, wherein:
   the retaining means comprises a gripper; and
   the transport mechanism comprises a control means including a cam gear for controlling the movement of the gripper.

5. The analytical system of claim 1, wherein:
   the retaining means comprises a gripper; and
   the gripper is coupled by an adjustment means to a lid that closes the magazine guide, such that the gripper moves to a release position when the lid is opened.

6. The analytical system of claim 1, wherein the magazine guide has three supporting portions which span one plane and which serve to support a plane guide surface of the magazine.

7. The analytical system of claim 1, wherein the magazine, movable to a limited extent in a bearing plane, is under the influence of a force perpendicular to the bearing plane.

8. The analytical system of claim 1, wherein the active magazine unit is located in front of a measurement unit, and the second transport element is at a distance much farther away from the first transport element than the first transport element from the measurement unit.

9. The analytical system of claim 1, wherein the second transport element is diametrically opposite to the first transport element of the active magazine unit.

10. A method for the operation of the analytical system of claim 1, comprising: inserting the magazine in the magazine guide of the hand-held device, transporting the magazine in steps in the magazine guide by the transport mechanism that engages on the transport elements, optionally arranged in a ring shape, and bringing the retaining means of the fixing mechanism into engagement with the transport elements of the magazine units, wherein the active magazine unit provided for use is positioned in a predefined functional position in the device.

11. The method of claim 10, wherein the magazine, for onward indexing of the magazine units, is pivoted about an individual bearing point fixed on the device and is released therefrom, wherein the transport element of the respective active magazine unit is guided in the bearing point, and the transport elements of the other magazine units are moved against a directing contour of the magazine guide.

* * * * *